Figure 1:
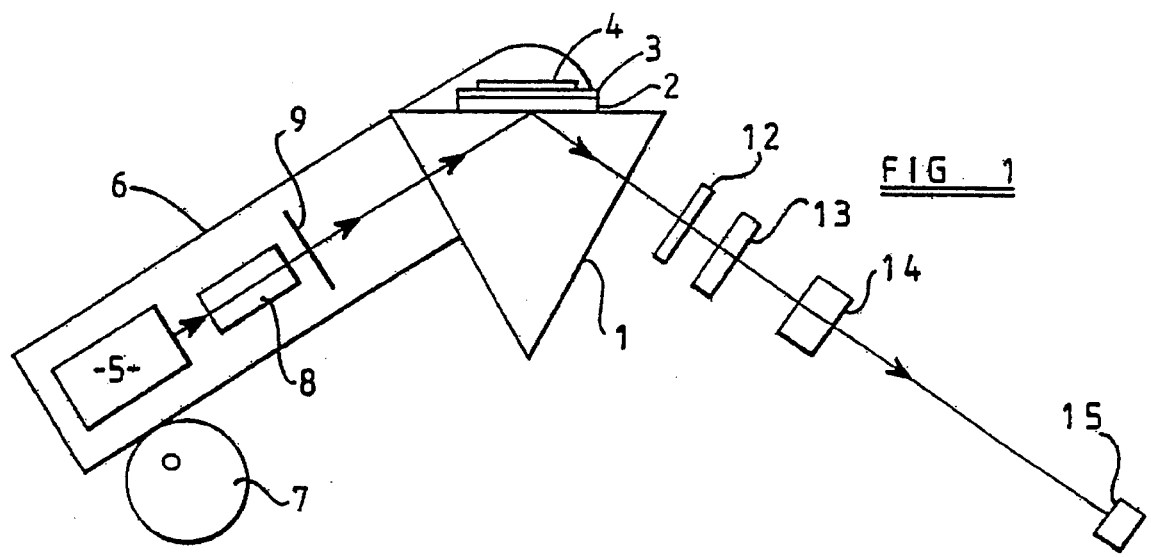

United States Patent

Stewart et al.

[11] Patent Number: 5,491,556
[45] Date of Patent: Feb. 13, 1996

[54] ANALYTICAL DEVICE WITH VARIABLE ANGLE OF INCIDENCE

[75] Inventors: Douglas A. Stewart; Colin H. Maule, both of Cambridge; James O. Molloy, Newmarket, all of United Kingdom

[73] Assignee: Fisons, plc, United Kingdom

[21] Appl. No.: 256,385

[22] PCT Filed: Jan. 8, 1993

[86] PCT No.: PCT/GB93/00025

§ 371 Date: Jul. 8, 1994

§ 102(e) Date: Jul. 8, 1994

[87] PCT Pub. No.: WO93/14391

PCT Pub. Date: Jul. 22, 1993

[30] Foreign Application Priority Data

Jan. 11, 1992 [GB] United Kingdom ............... 9200564

[51] Int. Cl.⁶ .................................................. G01N 21/55
[52] U.S. Cl. ............................................ 356/445; 356/128
[58] Field of Search ............................ 356/445, 128, 356/136

[56] References Cited

U.S. PATENT DOCUMENTS

| | | | |
|---|---|---|---|
| 4,142,797 | 3/1979 | Astheimer | 356/363 |
| 4,877,747 | 10/1989 | Stewart | 436/525 |
| 5,023,053 | 6/1991 | Finlan | 356/445 |

FOREIGN PATENT DOCUMENTS

| | | |
|---|---|---|
| 0305109 | 3/1989 | European Pat. Off. |
| 0341927 | 11/1989 | European Pat. Off. |
| 2254415 | 10/1992 | United Kingdom |
| WO87/00617 | 1/1987 | WIPO |
| WO90/05295 | 5/1990 | WIPO |
| WO91/13339 | 9/1991 | WIPO |
| WO92/05426 | 4/1992 | WIPO |

OTHER PUBLICATIONS

Patent Abstracts of Japan, vol. 12, No. 88, 23 Mar. 1988.

*Primary Examiner*—Richard A. Rosenberger
*Attorney, Agent, or Firm*—Nixon, Hargrave, Devans & Doyle

[57] ABSTRACT

Apparatus for the determination of a chemical or biochemical species comprises a resonant optical biosensor (1–4) disposed in a light path between a pivotally-mounted source (5) of monochromatic light and a stationary detector (12) adapted to monitor some characteristic of the light. There is provided means (7) for causing pivotal motion of the light source (5) so as to vary the angle of incidence of the light on the sensor (1–4). Also provided is means for monitoring the instantaneous angle of incidence. The means for varying the angle of incidence of the light on the sensor may be a cam arrangement (7) acting on a pivoting member (6) carrying the light source (5), and the means for monitoring the instantaneous angle of incidence of the light on the sensor (1–4) may comprise means for monitoring the number of steps performed by a stepper motor driving the cam arrangement (7).

5 Claims, 1 Drawing Sheet

ANALYTICAL DEVICE WITH VARIABLE ANGLE OF INCIDENCE

This invention relates to sensors, especially those termed biosensors, ie devices for the analysis of biologically active species such as antigens and antibodies in samples of biological origin. In particular, the invention relates to biosensors based on resonant optical phenomena, eg surface plasmon resonance or resonant attenuated or frustrated total internal reflection.

Many devices for the automatic determination of biochemical analytes in solution have been proposed in recent years. Typically, such devices (biosensors) include a sensitised coating layer which is located in the evanescent region of a resonant field. Detection of the analyte typically utilizes optical techniques such as, for example, surface plasmon resonance (SPR), and is based on changes in the thickness and/or refractive index of the coating layer resulting from interaction of that layer with the analyte. This causes a change, eg in the angular position of the resonance.

Other optical biosensors include a waveguide in which a beam of light is propagated. The optical characteristics of the device are influenced by changes occurring at the surface of the waveguide. One form of optical biosensor is based on frustrated total reflection. The principles of frustrated total reflection (FTR) are well-known; the technique is described, for example, by Bosacchi and Oehrle [Applied Optics (1982), 21, 2167–2173]. An FTR device for use in immunoassay is disclosed in European Patent Application No 0205236A and comprises a cavity layer bounded on one side by the sample under investigation and on the other side by a spacer layer which in turn is mounted on a substrate. The substrate-spacer layer interface is irradiated with monochromatic radiation such that total reflection occurs, the associated evanescent field penetrating through the spacer layer. If the thickness of the spacer layer is correct and the incident parallel wave vector matches one of the resonant mode propagation constants, the total reflection is frustrated and radiation is coupled into the cavity layer. The cavity layer must be composed of material which has a higher refractive index than the spacer layer and which is transparent at the wavelength of the incident radiation.

In devices of this kind, the position of resonance is monitored by varying the angle at which light is incident on the sensor. The scanning of angle may be performed either sequentially or simultaneously ie by varying the angle of incidence of a parallel beam of light or by simultaneously irradiating over a range of angles using a fan-shaped beam of light as described (in connection with SPR) in European Patent Application No 0305109A. In the former case, prior proposals have involved a single-channel detector which is mechanically scanned over a range of angles; this necessitates synchronisation of the movement of the light source and the detector. In the latter case, in which a range of angles is irradiated simultaneously, it is generally necessary to use a multi-channel detector having angular resolution. This leads to relatively high manufacturing costs.

There has now been devised an apparatus involving the use of a resonant optical sensor for the determination of a chemical or biochemical species, which overcomes or substantially mitigates some or all of the disadvantages of the prior art arrangements described above.

According to the invention, there is provided apparatus for the determination of a chemical or biochemical species, comprising a resonant optical biosensor disposed in a light path between a pivotally-mounted source of monochromatic light and a stationary detector adapted to monitor some characteristic of the light, there being provided means for causing pivotal motion of the light source so as to vary the angle of incidence of the light on the sensor and means for monitoring the instantaneous angle of incidence.

The apparatus according to the invention is advantageous primarily in that it is of relatively simple construction and uses only a single-channel detector. Also, the means for monitoring the instantaneous angle of incidence provides an accurate correlation of the output characteristics of the light beam with that angle.

Any convenient source of monochromatic light may be used. The choice of source will depend inter alia on the particular form of sensor used. In this context, 'light' may include not only visible light but also wavelengths above and below this range, eg in the ultra-violet and infra-red.

The means for varying the angle of incidence of the light on the sensor may be mechanical, eg a stepper motor-driven cam arrangement acting on a pivoting member carrying the light source and associated optics. The angle of incidence is preferably varied over only that range of angles in which resonance occurs.

The means for monitoring the instantaneous angle of incidence of the light on the sensor may comprise means for monitoring the number of steps performed by a stepper motor driving the cam arrangement, the relationship between the cam position and the angle of incidence being known. A non-contact zero position indicator may be used on the cam arrangement to ensure that the stepper motor is performing as expected.

The characteristic of the light which is monitored may be any characteristic which changes at resonance, eg the phase of reflected radiation or, in some cases, the intensity.

The sensor is preferably an FTR sensor. Such a sensor will generally include an optical structure comprising a) a cavity layer of transparent dielectric material of refractive index $n_3$, b) a dielectric substrate of refractive index $n_1$, and c) interposed between the cavity layer and the substrate, a dielectric spacer layer of refractive index $n_2$.

In use, the interface between the substrate and the spacer layer is irradiated with light such that internal reflection occurs. Resonant propagation of a guided mode in the cavity layer will occur, for a given wavelength, at a particular angle of incidence of the exciting radiation.

The angular position of the resonant effect depends on various parameters of the sensor device, such as the refractive indices and thicknesses of the various layers. In general, it is a pre-requisite that the refractive index $n_3$ of the cavity layer and the refractive index $n_1$ of the substrate should both exceed the refractive index $n_2$ of the spacer layer. Also, since at least one mode must exist in the cavity to achieve resonance, the cavity layer must exceed a certain minimum thickness.

The cavity layer is preferably a thin-film of dielectric material. Suitable materials for the cavity layer include zirconium dioxide, titanium dioxide, aluminium oxide and tantalum oxide.

The cavity layer may be prepared by known techniques, eg vacuum evaporation, sputtering, chemical vapour deposition or in-diffusion.

The dielectric spacer layer must have a lower refractive index than both the cavity layer and the substrate. The layer may, for example, comprise an evaporated or sputtered layer of magnesium fluoride. In this case an infra-red light injection laser may be used as light source. The light from such a source typically has a wavelength around 800 nm. Other suitable materials include lithium fluoride and silicon dioxide. Apart from the evaporation and sputtering techniques mentioned above, the spacer layer may be deposited on the substrate by a sol-gel process, or be formed by chemical reaction with the substrate.

The sol-gel process is particularly preferred where the spacer layer is of silicon dioxide.

The refractive index of the substrate ($n_1$) must be greater than that ($n_2$) of the spacer layer but the thickness of the substrate is generally not critical.

By contrast, the thickness of the cavity layer must be so chosen that resonance occurs within an appropriate range of coupling angles. The spacer layer will typically have a thickness of the order of several hundred nanometres, say from about 200 nm to 2000 nm, more preferably 500 to 1500 nm, eg 1000 nm. The cavity layer typically has a thickness of a few tens of nanometres, say 10 to 200 nm, more preferably 30 to 150 nm, eg 100 nm.

It is particularly preferred that the cavity layer has a thickness of 30 to 150 nm and comprises a material selected from zirconium dioxide, titanium dioxide, tantalum oxide and aluminium oxide, and the spacer layer has a thickness of 500 to 1500 nm and comprises a material selected from magnesium fluoride, lithium fluoride and silicon dioxide, the choice of materials being such that the refractive index of the spacer layer is less than that of the cavity layer.

Preferred materials for the cavity layer and the spacer layer are tantalum oxide and silicon dioxide respectively.

At resonance, the incident light is coupled into the cavity layer by FTR, propagates a certain distance along the cavity layer, and couples back out (also by FTR). The propagation distance depends on the various device parameters but is typically of the order of 1 or 2 mm.

At resonance the reflected light will undergo a phase change, and it is this which may be detected. Alternatively, as described in our co-pending International Patent Application No PCT/GB91/01161 the cavity layer and/or spacer layer may absorb at resonance, resulting in a reduction in the intensity of the reflected light.

For use in the determination of biochemical species, the surface of the sensor, ie the surface of the cavity layer in the case of an FTR sensor, will generally be sensitised by having biomolecules, eg specific binding partners for the analyte(s) under test, immobilised upon it. The immobilised biochemicals may be covalently bound to the sensor surface by methods which are well known to those skilled in the art.

Figure 2:
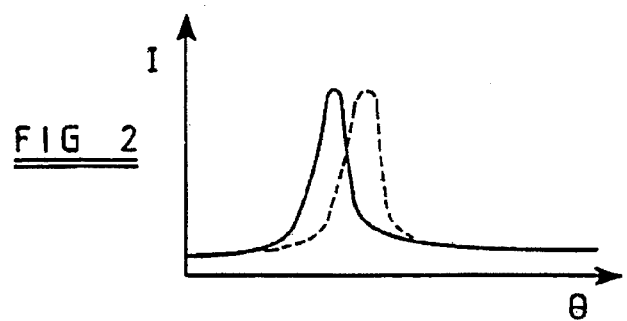
Figure 3:
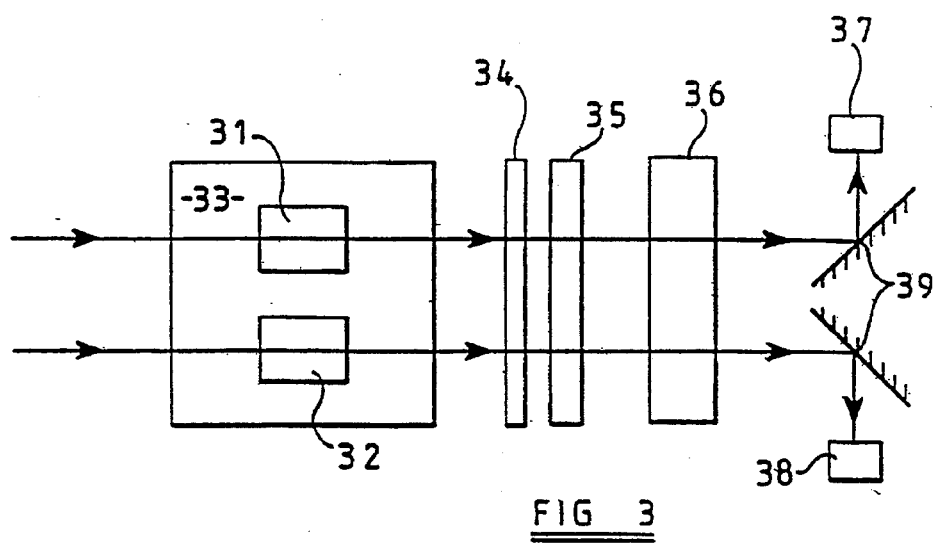

The invention will now be described in more detail, by way of illustration only, with reference to the accompanying drawings in which FIG. 1 is a schematic view (not to scale) of an apparatus according to the invention, FIG. 2 depicts the dependence of the intensity of the detected light on the angle of incidence, and FIG. 3 is a plan view of part of a second embodiment of an apparatus according to the invention in which two regions of a sensor are irradiated simultaneously.

Referring first to FIG. 1, a biosensor comprises a glass prism 1 coated over an area of its base with a first coating 2 of magnesium fluoride and a second coating 3 of titanium dioxide. The prism 1 and first and second coatings 2,3 together constitute a resonant optical structure, the first coating 2 acting as a spacer layer and the second coating 3 as a cavity layer. The first coating 2 has a thickness of approximately 1000 nm and the second coating 3 a thickness of approximately 100 nm.

Immobilised on the surface of the second coating 3 is a layer 4 of immobilised biochemicals, which act as specific binding partner for the analyte under test.

The interface between the base of the prism 1 and the first coating 2 is irradiated by a beam of monochromatic light from a laser 5 which is mounted on a pivoted arm 6. The arm 6 can be moved through a range of angles by means of a cam 7 which is driven by a stepper motor (not shown).

Also mounted on the arm 6, between the laser 5 and the prism 1, are collimating optics 8 and a polariser 9. The polariser 9 is arranged to produce linearly polarised light with two components: transverse electric (TE) and transverse magnetic (TM). The polariser is set at 45° to the TE and TM transmission axes and thus provides equal components of TE and TM light.

All the light incident on the interface between the base of the prism 1 and the first coating 2 is reflected, resonance being detected as a change of phase of the reflected light.

The reflected light is passed through a compensator 12 to a polarisation analyser 13. The compensator 12, which may be of any conventional form, is manually adjusted to remove any phase difference which is introduced into the TE and TM components on reflection and by birefringence in the optical path.

The analyser 13 is arranged at 90° to the polariser 9. The TE and TM components are interfered at the analyser to allow the phase change to be detected. Off resonance both components undergo a similar phase shift on reflection and the relative phase between the components is adjusted by the compensator 12 to give zero transmission through the analyser 13. This will apply for all angles except near resonance. Near resonance of either component, the phase shift between the TE and TM components will vary rapidly with angle, resulting in maximum throughput of light through the analyser 13 at resonance.

Light passing through the analyser 13 is focussed by a cylindrical condenser lens arrangement 14 onto a detector 15. The condenser lens arrangement 14 is located so as to collect light from all incident angles onto the detector 15. This minimises the effects of positioning errors.

In use, the angle of incidence of light on the interface between the base of the prism 1 and the first coating layer 2 is varied by rotation of the cam 7. The incident light beam is therefore scanned through a range of incident angles including the resonant angle. Off-resonance no light intensity is detected at the detector 15; as resonance is approached, the detected light intensity increases and then falls. The increase in intensity is correlated with the angle of incidence, enabling the angular position of the resonance to be determined. The instantaneous angle of incidence is determined from the instantaneous position of the cam 7, the relationship between the cam position and the angle of incidence being known.

When the layer of immobilised biochemicals 4 is contacted with a sample containing the analyte under test, specific binding occurs between the biochemicals and the analyte molecules, resulting in a change in the refractive index in the vicinity of the surface of the device. This in turn results in a shift in the position of the resonance. FIG. 2 shows a plot of the measured signal intensity against angle of incidence before and (dotted line) after complexation of the immobilised biochemicals with the analyte.

In the embodiment shown in FIG. 3, there are two separate patches 31,32 of immobilised biochemicals on the surface of the prism 33. Each patch 31,32 is irradiated with a separate beam of incident radiation, the angle of incidence being scanned as described above.

Each reflected beam is passed through a compensator 34 and a polarisation analyser 35, and then focussed by a cylindrical condenser lens arrangement 36 onto two detectors 37,38. Again, the lens arrangement 36 is located so as to collect light from all incident angles onto the corresponding detector 37,38. The cylindrical condenser lens arrangement 36 has power only in one dimension, thereby preserving the spatial separation of the light beams reflected from the separate patches 31,32.

As shown in FIG. 3, reflecting mirrors 39 are placed in the beam to enable the detectors 37,38 to be spatially separated.

We claim:

1. Apparatus for the determination of a chemical or biochemical species, said apparatus comprising a pivotally-mounted source of monochromatic light, a stationary detector adapted to monitor a characteristic of the light, a resonant optical biosensor disposed in a light path between said source and said detector, means for causing pivotal motion of said source so as to vary the angle of incidence of the light on said sensor, and means for monitoring the instantaneous angle of incidence of the light on said sensor, wherein said resonant optical biosensor is a frustrated total reflection sensor comprising:

a cavity layer of transparent dielectric material of refractive index $n_3$, a dielectric substrate of refractive index $n_1$, and interposed between said cavity layer and said substrate, a dielectric spacer layer of refractive index $n_2$, wherein $n_2$ is less than $n_1$ and $n_2$ is less than $n_3$.

2. Apparatus as claimed in claim 1, wherein the angle of incidence is variable only over that range of angles in which resonance occurs.

3. Apparatus as claimed in claim 1, wherein said means for causing pivotal motion of said source comprises a cam arrangement acting on a pivoting member carrying said source.

4. Apparatus as claimed in claim 3, wherein said means for monitoring the instantaneous angle of incidence of the light on said sensor comprises means for monitoring the number of steps performed by a stepper motor driving said cam arrangement.

5. Apparatus as claimed in claim 3, further comprising a non-contact zero position indicator for said cam arrangement.

* * * * *